US010357531B2

(12) United States Patent
Harti et al.

(10) Patent No.: US 10,357,531 B2
(45) Date of Patent: Jul. 23, 2019

(54) METHOD FOR THE MANAGEMENT OF CANCER AND CANCER TREATMENT-RELATED COMORBIDITIES

(71) Applicant: LEGACY HEALTHCARE LTD., Valleta (MT)

(72) Inventors: Saad Harti, Lutry (CH); JiaWei Liu, Geneva (CH)

(73) Assignee: Legacy Healthcare Ltd., Valleta Vlt (MT)

( * ) Notice: Subject to any disclaimer, the term of this patent is extended or adjusted under 35 U.S.C. 154(b) by 245 days.

(21) Appl. No.: 15/032,179

(22) PCT Filed: Nov. 7, 2014

(86) PCT No.: PCT/EP2014/074048
§ 371 (c)(1),
(2) Date: Apr. 26, 2016

(87) PCT Pub. No.: WO2015/067759
PCT Pub. Date: May 14, 2015

(65) Prior Publication Data
US 2016/0256512 A1 Sep. 8, 2016

Related U.S. Application Data

(60) Provisional application No. 61/901,631, filed on Nov. 8, 2013.

(51) Int. Cl.
| | | |
|---|---|---|
| *A61K 36/752* | (2006.01) |
| *A61K 36/88* | (2006.01) |
| *A61K 36/77* | (2006.01) |
| *A61K 36/8962* | (2006.01) |
| *A61K 36/185* | (2006.01) |
| *A61K 31/352* | (2006.01) |
| *A61K 36/18* | (2006.01) |

(52) U.S. Cl.
CPC ............ *A61K 36/88* (2013.01); *A61K 31/352* (2013.01); *A61K 36/18* (2013.01); *A61K 36/185* (2013.01); *A61K 36/752* (2013.01); *A61K 36/77* (2013.01); *A61K 36/8962* (2013.01)

(58) Field of Classification Search
None
See application file for complete search history.

(56) References Cited

U.S. PATENT DOCUMENTS

| | | | |
|---|---|---|---|
| 5,773,241 A | 6/1998 | Ericsson | |
| 6,582,702 B2 * | 6/2003 | Rigby | A61K 36/185 424/195.18 |
| 7,157,109 B2 * | 1/2007 | Kipfer | A23L 2/02 426/478 |
| 8,088,431 B2 * | 1/2012 | Ward | A23G 1/32 426/631 |
| 8,361,522 B2 | 1/2013 | Ulmann et al. | |
| 8,652,543 B2 | 2/2014 | Ulmann et al. | |
| 2003/0077336 A1 | 4/2003 | Maffetone | |
| 2004/0076614 A1 | 4/2004 | Schur | |
| 2006/0018867 A1 | 1/2006 | Kawasaki et al. | |
| 2008/0305096 A1 | 12/2008 | Verdegem et al. | |
| 2010/0104671 A1 * | 4/2010 | Ulmann | A61K 8/27 424/736 |
| 2010/0154144 A1 | 6/2010 | Guerin et al. | |
| 2012/0064174 A1 | 3/2012 | Harti et al. | |
| 2013/0108719 A1 | 5/2013 | Ulmann et al. | |
| 2013/0323334 A1 | 12/2013 | Harti | |
| 2016/0263012 A1 | 9/2016 | Harti | |

FOREIGN PATENT DOCUMENTS

| | | | |
|---|---|---|---|
| CH | 682217 | A5 | 8/1993 |
| DE | 2844614 | A1 | 5/1980 |
| DE | 19533777 | A1 | 3/1997 |
| DE | 202004012348 | U1 | 10/2004 |
| DE | 102004011968 | A1 | 9/2005 |
| DE | 102005010142 | A1 | 11/2005 |
| EP | 0467660 | A2 | 1/1992 |
| FR | 2706771 | A1 | 12/1994 |
| FR | 2865132 | A1 | 7/2005 |
| FR | 2877219 | A1 | 5/2006 |

(Continued)

OTHER PUBLICATIONS

Abdullah, Fadwah et al., "Alopecia: Botanical Approaches in Review." Journal of Drugs in Dermatology, vol. 9, No. 5, pp. 537-541, May 2010.

Aktas, Aynur et al., "Symptom clusters: myth or reality?" Palliative Medicine, vol. 24, No. 4, pp. 373-385, 2010.

Bower, Julienne E. et al., "Inflammation and cancer-related fatigue: Mechanisms, contributing factors, and treatment implications." Brain, Behavior, and Immunity, vol. 30, No. 0, pp. S48-S57, Mar. 2013.

Bower, Julienne E., "Cancer-related fatigue: Links with inflammation in cancer patients and survivors." Brain, Behavior, and Immunity, vol. 21, pp. 863-871, 2007.

(Continued)

Primary Examiner — Susan Hoffman
(74) Attorney, Agent, or Firm — Harness, Dickey & Pierce, PLC

(57) ABSTRACT

A method for the management of cancer and treatment of cancer comorbidities, including but not limited to cancer-related fatigue, cachexia, anorexia, pain, anemia, asthenia, depression, muscle weakness, nausea, vomiting, skin, and skin appendages adverse reactions; the method including the administration by the conventional and non-conventional oral, topical, parenteral routes and intra-tumoral injection, or in combination thereof, or the administration as adjuvant potentiator in other therapies using the forenamed routes, of a composition containing as active ingredient an extract of *Allium* species, which contains querceting, an extract of *Citrus* species and an extract of *Paullinia* species and an extract of *Theobroma* species.

4 Claims, 2 Drawing Sheets

(56) References Cited

FOREIGN PATENT DOCUMENTS

| | | | |
|---|---|---|---|
| FR | 2877576 A1 | 5/2006 |
| JP | H08268863 A | 10/1996 |
| JP | H09194334 A | 7/1997 |
| JP | 2000044439 A | 2/2000 |
| JP | 2000247830 A | 9/2000 |
| JP | 2003201229 A | 7/2003 |
| JP | 2006104098 A | 4/2006 |
| JP | 2006342120 A | 12/2006 |
| KR | 20070022018 A | 2/2007 |
| WO | WO-2005120452 A1 | 12/2005 |
| WO | WO-2008015341 A2 | 2/2008 |
| WO | WO 2008/113912 A2 | * | 9/2008 |
| WO | WO 2012/113820 A1 | * | 8/2012 |
| WO | WO-2012140013 A2 | 10/2012 |
| WO | WO-2013/020719 A2 | 2/2013 |

OTHER PUBLICATIONS

Bower, Julienne E., "Cancer-related fatigue: Mechanisms, risk factors, and treatments." Nature Reviews Clinical Oncology, vol. 11, No. 10, pp. 597-609, 2014.
Carroll, Jennifer K. et al., "Pharmacologic Treatment of Cancer-Related Fatigue." The Oncologist, vol. 12 (Supplement 1), pp. 43-51, 2007.
Dorman, Will B., "Perfumes." Good Housekeeping, vol. 6, Nov. 12, 1887-Apr. 28, 1888, Clark W. Bryan and Co.: Massachusetts, p. 191, 1888.
Fan, G. et al., "Symptom clusters in cancer patients: a review of the literature." Current Oncology, vol. 14, No. 5, pp. 173-179, 2007.
Fiorentino, Lavinia et al., "The Symptom Cluster of Sleep, Fatigue and Depressive Symptoms in Breast Cancer Patients: Severity of the Problem and Treatment Options." Drug Discovery Today: Disease Models, vol. 8, No. 4, pp. 167-173, 2011.
Paus, R. et al., "Telogen skin contains an inhibitor of hair growth." British Journal of Dermatology, vol. 122, pp. 777-784, 1990.
Puri, Neerja et al., "A Study of Nail Changes in Various Dermatosis in Punjab, India." Our Dermatology Online, vol. 3, No. 3, pp. 164-170, 2012.
Tavio, Marcello et al., "Cancer-related fatigue (Review)." International Journal of Oncology, vol. 21, pp. 1093-1099, 2002.
Tzia, C. et al., Extraction Optimization in Food Engineering, National Technical University of Athens, p. 194. 2005.
Wang, Xin Shelley et al., "Cancer-Related and Treatment-Related Fatigue." Gynecologic Oncology, vol. 136, No. 3, pp. 446-452, Mar. 2015.
Wang, Xin Shelley, "Pathophysiology of Cancer-Related Fatigue." Clinical Journal of Oncology Nursing, vol. 12, No. 5 (Supplemental), pp. 11-20, Oct. 2008.

* cited by examiner

METHOD FOR THE MANAGEMENT OF CANCER AND CANCER TREATMENT-RELATED COMORBIDITIES

CROSS-REFERENCE TO RELATED APPLICATIONS

This application is a National Phase Entry of International Patent Application No. PCT/EP2014/074048, filed on Nov. 7, 2014, which claims priority to U.S. Ser. No. 61/901,631, filed on Nov. 8, 2013, both of which are incorporated by reference herein.

TECHNICAL FIELD

The invention concerns a method for the management of cancer and treatment cancer comorbidities, including but not limited to cancer-related fatigue, cachexia, anorexia, pain, anemia, asthenia, depression, impaired cognitive function, loss of appetite, muscle weakness, nausea, vomiting, arthritis, organ damage, including but not limited to radiation-induced burns, heart disorders due to cardiotoxicity by chemo- and radiotherapy, hypertension, thromboembolism, occasional chest pain, difficulty in breathing, shortness of breath, dizziness, fainting, pallor (pale skin or lips), headaches, difficulty in concentrating, insomnia, difficulty in staying warm, bleeding problems, nail damages, and skin appendages adverse reactions, exampled by irritation and dry skin, sore and dry ulcerated mouths.

BACKGROUND

So far, the main anti-cancer therapeutic strategies have consisted in inhibiting the non-controlled cell proliferation. Nonetheless, as tumour evolution has multifaceted mechanisms, more strategies should be considered in order to address the remaining gaps in cancer management, and more importantly in alleviating the side effects of cancer treatments. Previous research indicates that inflammatory cells and pro-inflammatory molecules mostly contribute to tumor growth and progression. In experimental settings, reduction of inflammatory molecules (e.g. cytokines) inhibits cancer development. Based on earlier research, blockade of inflammation appears to be a relevant strategy for management of cancer. Therefore, controlling or reducing such a process of "malignant flame" (inflammation) represents a crucial approach in the management of cancer.

Anticancer therapies have extended patients' life expectancy; however, cancer-related and its treatment-related comorbidities have become an issue for cancer survivors. The above mentioned disorders are among the most feared side-effects of anticancer agents so that the quality of life (QoL), as well as the life expectancy might be countered by reduced QoL and increased mortality.

Asthenia fatigue syndrome (AFS) or cancer-related fatigue is a common symptom perceived during and after treatment by patients with cancer and consists of pathologic fatigue, poor endurance, and impaired motor and cognitive function. It is a symptom, difficult to define, with a set of vague sensations, different for each patient. Some studies in cancer have reported the findings about how the above-mentioned comorbidities can increase the severity of cancer related fatigue.

A growing body of research has examined the hypothesis that cancer-related fatigue is driven by activation of the pro-inflammatory cytokine network. Actually, inflammation appears to play an essential role in cancer-related fatigue before, during and after cancer therapies. Accordingly, controlling or reducing the persistent inflammatory process can be beneficial to the management of cancer related fatigue. The persistent pathological conditions in cancer patients may favour up-regulated expressions of pro-inflammatory mediators/cytokines and cause a sustained high level of chronic inflammation in the whole body, forming an important ground for triggering the comorbidities of cancer.

In the context of cancer treatment, anti-cancer chemoagents destroy rapidly dividing cancer cells, as well as all the fast dividing non-cancer cells, which undergo apoptosis due to chemotherapy agents and radiotherapy attack. The massive apoptosis of so many non-cancerous cells results in a large amount of secondary necrotic cells. These necrotic cells will cause and sustain inflammation by stimulating production of pro-inflammatory molecules.

Many internal and external factors can contribute to unwanted prolonged inflammation. However, activated vascular endothelial cells (ECs) in the human vasculature, as they are in direct contact with blood, play pivotal roles in the development of acute and chronic inflammation. Therefore, vascular EC may represent a relevant therapeutic target for the management of cancer and treatment of cancer comorbidities, including but not limited to cancer-related fatigue, cachexia, anorexia, pain, anemia, asthenia, depression, muscle weakness, nausea, vomiting, skin and skin appendages adverse reactions.

One of the possible mechanisms by which inflammation may contribute to the development of tumorgenesis includes enhanced expression of pro-inflammatory mediators such as cytokines (e.g. Interleukin 8) and adhesion molecules, e.g. ICAM-1 (Intercellular Adhesion Molecule 1, also known as CD54), E-selectin/ELAM-1 (also known as CD62E). The adhesion molecules can be found in low concentrations in the membranes of endothelial cells that "line" the interior surface of blood vessels in the whole vascular system. Their expression levels are essential in the inflammatory process. A lower expression of such pro-inflammatory molecules indicates lesser inflammation, while higher expression indicates augmented inflammatory status. Upon toxic or pathological insults, the produced TNF-alpha (Tumor Necrosis Factor) will greatly stimulate expression of adhesion molecules and cytokines exampled by E-selectin, ICAM-1 and Interleukin 8 (IL-8). Increased expressions of adhesion molecules and cytokines mediate immune and inflammatory responses via recruitment of leukocytes to inflammatory sites (infiltration of inflammatory cells through local vascular endothelium).

A former study showed that, compared with controls, the levels of soluble E-selectin and ICAM-1 were significantly higher in breast cancer patients at late stage. Besides, elevated adhesion molecule levels were predictive of decreased survival. In addition, various pro-inflammatory mediators may not only switch on the tumor-prone inflammatory angiogenesis, a process that is essentially controlled by vascular endothelial growth factor, but also promote tumor metastasis. Hence, for reducing harmful inflammation, it is critical to limit the synthesis of these pro-inflammatory molecules so as to decrease the anomalous inflammatory response.

Our studies show that, at molecular level, a composition comprising the ingredients mentioned hereafter is an anti-inflammatory agent, capable of reducing TNFα induced expression of adhesion molecules ICAM-1 and E-selectin on HUVECs (Human Umbilical Vein Endothelial Cells), as well as the cytokine IL-8 expression. Such anti-inflammatory potential results in inhibition of tumour progression and reduction of tumor size (see in the section above and data in the examples, obtained from both in vitro and in vivo studies). Thus, a composition comprising the ingredients mentioned hereafter provides anti-inflammatory effect for the support management of cancer and treatment of cancer comorbidities.

A composition comprising the ingredients mentioned hereafter was subcutaneously injected into a mouse cancer model in a randomized experiment. It was observed that, compared to non-treated mice, the composition inhibits tumor growth and tumor size in treated mice (see data in the example 2 obtained from both in vitro and in vivo studies). A composition comprising the ingredients mentioned hereafter was used in a topical formulation by cancer patients in order to prevent chemotherapy induced alopecia. Some patients reported that, apart from the beneficial effect on unwanted hair loss, other symptoms, such as fatigue, which they were also suffering from, started to improve steadily.

SUMMARY

A composition comprising the ingredients mentioned hereafter was used orally by a patient suffering from liver cancer. Based on the physicians and patient's report and pictures taken before and after the intake of the composition, his general state turned out to improve significantly, including alleviation of cancer related fatigue. It has been discovered that the administration by oral route, topical, or parenteral route, intra-tumoral injection, or a combination thereof, of a composition containing as active ingredient an extract of *Allium* species, which may contain quercetin, an extract of *Citrus* species and an extract of *Paullinia* species and an extract of *Theobroma* species, has a novel and previously unknown effect for the management of cancer and treatment of cancer comorbidities. The present invention proposes a method for the management of cancer and treatment of cancer comorbidities, including but not limited to cancer-related fatigue, cachexia, anorexia, pain, anemia, asthenia, depression, muscle weakness, nausea, vomiting, skin and skin appendages adverse reactions; comprising the administration by both conventional and non-conventional routes, and or as adjuvant potentiator in cell therapies, or topical route, or parenteral route, or intra-tumoral injection, or in combination, of a composition containing as active ingredient an extract of *Allium* species, which preferably contain quercetin, an extract of *Citrus* species and an extract of *Paullinia* species and an extract of *Theobroma* species.

DETAILED DESCRIPTION

Figure 1:
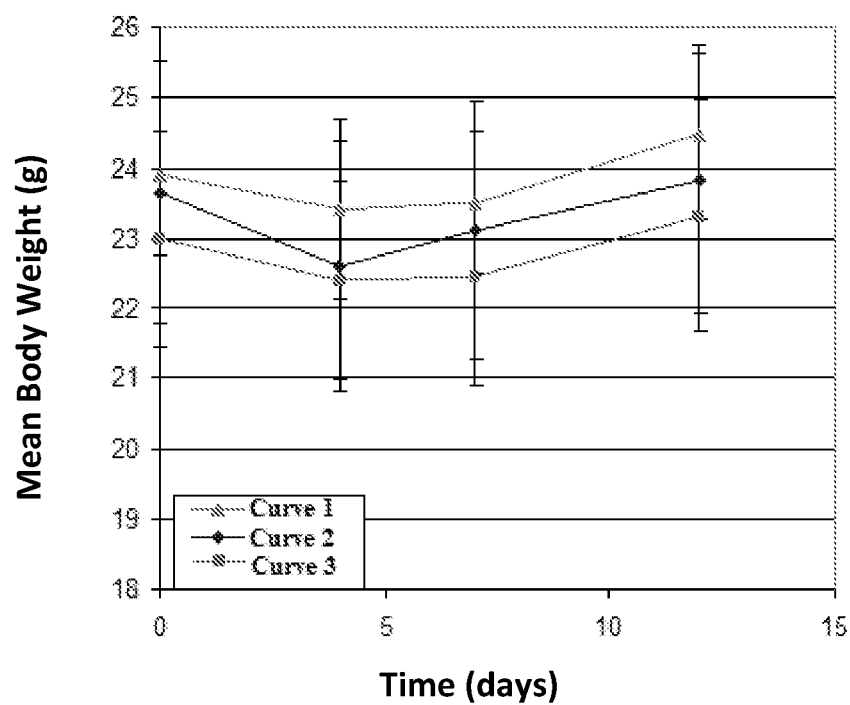
FIG. 1 corresponds to the curves of the mean body weight (in grams) measured at different times.

In particular, the present invention concerns a method for the management of cancer and treatment of cancer comorbidities, including but not limited to cancer-related fatigue, cachexia, anorexia, pain, anemia, asthenia, depression, impaired cognitive function, loss of appetite, muscle weakness, nausea, vomiting, arthritis, organ damage, including but not limited to radiation-induced burns, heart disorders due to cardiotoxicity by chemo- and radiotherapy, hypertension, thromboembolism, occasional chest pain, difficulty in breathing, shortness of breath, dizziness, fainting, pallor (pale skin or lips), headaches, difficulty in concentrating, insomnia, difficulty in staying warm, bleeding problems, nail damages, and skin appendages adverse reactions, exampled by irritation and dry skin, sore and dry ulcerated mouths; comprising the administration by oral route, topical, or parenteral route, intra-tumoral injection, or a combination thereof, of a composition containing as active ingredient an extract of *Allium* species, which may contain quercetin, an extract of *Citrus* species and an extract of *Paullinia* species and an extract of *Theobroma* species. Among the methods for the management of t cancer and treatment of cancer comorbidities, according to the invention, those which are of more particular interest are the methods in which the preferred oral composition contains from 30% to 93% by weight of an extract of *Allium* species, which contains quercetin, from 3% to 33% by weight of an extract of *Citrus* species, from 0.10% to 2.5% by weight of an extract (atomized or not) of *Paullinia* species and from 0.10% to 2.5% by weight of an extract (atomized or not) of *Theobroma* species, based on the total weight of the four active ingredients.

According to an embodiment, the composition comprises from 30% to 93% by weight of an extract of *Allium* species, which contains quercetin, from 3% to 33% by weight of an extract of *Citrus* species, from 0.10% to 2.5% by weight of an extract (atomized or not) of *Paullinia* species, from 0.10% to 2.5% by weight of an extract (atomized or not) of *Theobroma* species, from 0.5% to 3.0% by weight of Sodium chloride and from 25% to 50% by weight of Glycerin, based on the total weight of the composition. Among the methods for the management of cancer and treatment of cancer comorbidities, those which are the more preferred interest are the methods in which the compositions are used not only as conventional oral composition, composition for injection, topical application, but also as an adjuvant potentiator in for the management of cancer and its treatment-related comorbidities. The compositions contain from 30% to 93% by weight of an extract of *Allium* species, which contains quercetin, from 3% to 33% by weight of an extract of *Citrus* species, from 0.10% to 2.5% by weight of an extract (atomized or not) of *Paullinia* species and from 0.10% to 2.5% by weight of an extract (atomized or not) of *Theobroma* species, based on the weight of the four active ingredients.

According to an embodiment, the compositions contain from 30% to 93% by weight of an extract of *Allium cepa*, from 3% to 33% by weight of an extract of *Citrus lemon*, from 0.10% to 2.5% by weight of an extract (atomized or not) of *Paullinia* species and from 0.10% to 2.5% by weight of an extract (atomized or not) of *Theobroma* species, based on the weight of the four active ingredients. According to an embodiment, the composition contains from 30% to 93% by weight of an extract of *Allium* species, which contains quercetin, from 3% to 33% by weight of an extract of *Citrus* species, from 0.10% to 2.5% by weight of an extract (atomized or not) of *Paullinia* species, from 0.10% to 2.5% by weight of an extract (atomized or not) of *Theobroma* species, from 0.5% to 3.0% by weight of Sodium chloride and from 25% to 50% by weight of Glycerin, based on the total weight of the composition.

The term extract of *Allium* species refers particularly to extracts and native extracts obtained from all species of the genus *Allium* (family Liliaceae) and especially *Allium cepa*, which may contain quercetin. The term extract of *Citrus* species refers particularly to extracts and native extracts obtained from all species of the genus *Citrus* (family Rutaceae) and especially *Citrus lemon*. The term extract (atomised or not) of *Paullinia* species refers particularly to extracts and native extracts obtained from all species of the genus *Paullinia* (family Sapindaceae) and especially *Paullinia cupana*. The term extract (atomised or not) of *Theobroma* species refers particularly to aqueous-alcoholic extracts and native extracts obtained from all species of the genus *Theobroma* (family Malvaceae) and especially *Theobroma cacao*.

The most preferred compositions used according to the invention are: those containing approximately 87% by weight of an extract of *Allium cepa*, which contains quercetin, approximately 12% by weight of an extract of *Citrus* lemon, approximately 0.5% by weight of an extract (atomized or not) of *Paullinia cupana* and approximately 0.5% by weight of an extract (atomized or not) of *Theobroma cacao*, based on the total weight of the four active ingredients. According to the invention, the composition is chronically administered in a mixture containing as active ingredient an extract of *Allium* species, which contains quercetin, an extract of *Citrus* species and an extract of *Paullinia* species and an extract of *Theobroma* species. According to an embodiment of the invention the composition is administered daily during a period of several months or longer with a composition containing as active ingredient an extract of *Allium* species, which contains quercetin, an extract of *Citrus* species and an extract of *Paullinia* species and an extract of *Theobroma* species.

In order to obtain a measurable effect on the management of cancer and treatment of cancer comorbidities, it is necessary to perform the administration of the compositions chronically, preferably during at least 6 months. When using the compositions obtained according to the invention, doses may vary within relatively wide limits and must be set according to the person being treated and the condition concerned. Pharmaceutical compositions normally contain from 0.4 to 1000 mg, preferably from 2 to 400 mg, of active ingredients as defined above, in the form of dry extract.

The present invention also concerns a composition containing as active ingredient an extract of *Allium* species, which contains quercetin, an extract of *Citrus* species and an extract of *Paullinia* species and an extract of *Theobroma* species for use in the management of cancer and for the treatment of cancer comorbidities, including but not limited to cancer-related fatigue, cachexia, anorexia, pain, anemia, asthenia, depression, muscle weakness, nausea, vomiting, skin, and skin appendages adverse reactions; by both conventional and non-conventional routes, and/or as adjuvant potentiator in cell therapies, or topical route, or parenteral route, or intra-tumoral injection, or in combination thereof. According to an embodiment of the invention the composition for use in the management of cancer and for the treatment of cancer comorbidities contains an extract of *Allium* species, which contains quercetin, an extract of *Citrus* species and an extract (atomized or not) of *Paullinia* species and an extract (atomized or not) of *Theobroma* species. According to a further embodiment of the invention the composition for use in the management of cancer and for the treatment of cancer comorbidities, contains from 30% to 93% by weight of an extract of *Allium* species, which contains quercetin, from 3% to 33% by weight of an extract of *Citrus* species, from 0.10% to 2.5% by weight of an extract (atomized or not) of *Paullinia* species and from 0.10% to 2.5% by weight of an extract (atomized or not) of *Theobroma* species, based on the total weight of the four active ingredients.

Example of the Treatment

The patients have received, every day by oral, topical, parenteral routes, or intra-tumoral injection, alone or in combination, a treatment containing:

an extract of *Allium cepa* (containing querceting): 87.04% an extract of *Citrus* lemon: 11.96% an atomised extract of *Paullinia* cupana: 0.50% an atomised extract of *Theobroma cacao*: 0.50%

(hereafter composition A).

This lotion has been prepared as indicated in example 1 of patent application WO 2008/113912. Composition A which is a mixture of four natural ingredients has been reported to beneficially affect defects in abnormal cell apoptosis, as well as in inflammatory processes. This has indicated that composition A is capable of affecting positively in the management of the above-mentioned cancer and cancer treatment related comorbidities.

Example 1

Study of the composition, containing as active ingredient an extract of *Allium* species, which contains quercetin, an extract of *Citrus* species and an extract of *Paullinia* species and an extract of *Theobroma* species, on its anti-inflammatory effect via inhibiting TNF alpha-induced expression of pro-inflammatory molecules: ICAM-1, E-selectin and Interleukin 8, as summarized Table 2a, 2b and 2c).

TABLE 1

The tested compositions

| Compound | Ingredient | in total % wt |
|---|---|---|
| A | *Allium Cepa* | 50.0 |
|  | *Citrus* | 50.0 |
| B | *Allium Cepa* | 87.5 |
|  | *Citrus* | 12.5 |
| C | *Allium Cepa* | 87.0 |
|  | *Citrus* | 12.0 |
|  | Guarana dry extract | 0.5 |
|  | Cacao dry extract | 0.5 |
| Control | Medium |  |

TABLE 2a

The effects of "compositions" on the expression of adhesion molecule ICAM-1 (CD54) on the surface of endothelial cells (HUVECs)

| Composition | Non-treated cells measured by sABC* | TNF-treated cells measured by sABC* | % Increase (+) % Reduction (−) compared to control |
|---|---|---|---|
| Medium (control) | 3 172 | 386 181 |  |
| A | 2 061 | 296 561 | −23% |
| B | 1 947 | 297 444 | −23% |
| C | 1 664 | 254 171 | −34% |

*specific Antibody Bound per Cell

TABLE 2b

The effects of "compositions" on the expression of
adhesion molecule E-selectin/ELAM-1 (CD62E) on the surface of
endothelial cells (HUVECs)

| Composition | Non-treated cells measured by sABC* | TNF-treated cells measured by sABC* | % Increase (+) % Reduction (−) compared to control |
|---|---|---|---|
| Medium (control) | Non detectable | 3 074 | |
| A | 251 | 4 235 | +38% |
| B | 186 | 3 447 | +12% |
| C | 65 | 1 648 | −46% |

*specific Antibody Bound per Cell

TABLE 2c

The effects of "compositions" on the expression of
cytokine Interleukin 8 (IL-8) by endothelial cells (HUVECs)

| Composition | Non-treated cells measured by sABC* | TNF-treated cells measured by sABC* | % Increase (+) % Reduction (−) compared to control |
|---|---|---|---|
| Medium (control) | 1 164 | 5 406 | |
| A | 1 067 | 6 274 | +16% |
| B | 1 015 | 5 563 | +3% |
| C | 887 | 4 827 | −11% |

*specific Antibody Bound per Cell

Example 2

Study on the anti-tumor activity of a new "composition" using nude mice carrying subcutaneous human tumor of type KB. FIG. 1 illustrates the curves of the average weight of nude mice bearing subcutaneous human tumor type KB. Mice were randomized at Day 7 and received a daily injection of 100 μl composition solution (THI) of 0.3% and 1.0% respectively for five consecutive days.

In FIG. 1, x-axis represents time (days); y-axis represents average weight of nude mice (g). Blue (curve 2): control vehicle; Pink (curve 3): composition (THI) of 0.3%; Yellow (curve 1): composition (THI) of 1%. No significant weight changes were observed.

Figure 2:
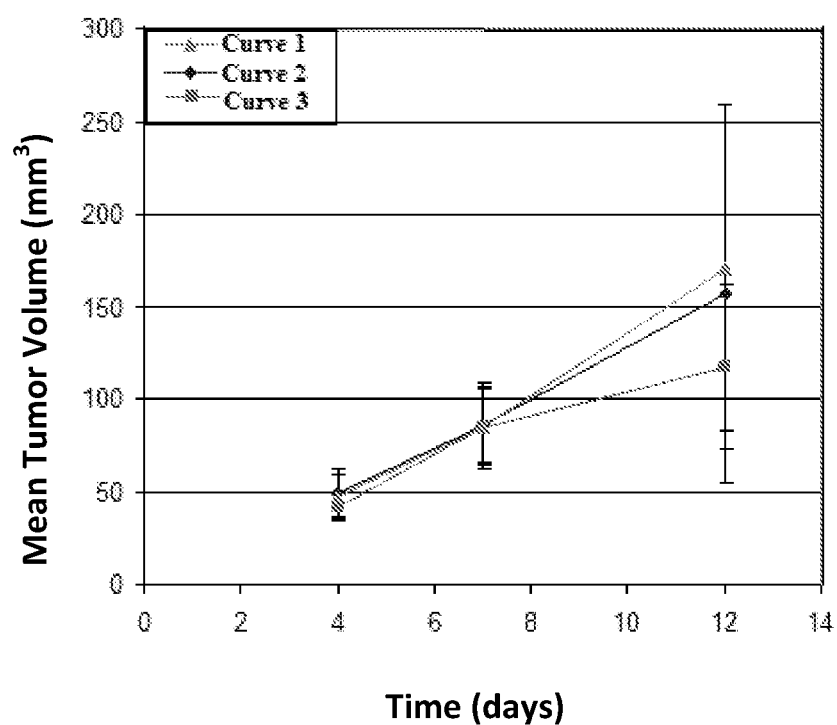
FIG. 2 corresponds to the curves of the mean tumor volume (in $mm^3$) measured at different times.

FIG. 2 illustrates the curves of the mean tumor volume of nude mice bearing subcutaneous human tumor type KB. Mice were randomized at Day 7 and received a daily injection of 100 μl composition solution (THI) of 0.3% and 1.0% respectively for five consecutive days. In FIG. 2, x-axis represents time (days); y-axis represents average tumor volume of nude mice (mm3). Blue (curve 2): control vehicle; Pink (curve 3): composition (THI) of 0.3%; Yellow (curve 1): composition (THI) of 1%. No significant weight changes were observed. Composition (THI) 0.3% show anti-tumor effect compared to control.

The invention claimed is:

1. A method for management of cancer and for treatment of cancer-related fatigue in a subject in need thereof, the method comprising:
    administering to the subject, by an oral route, a topical route, a parenteral route, an intra-tumoral injection, or a combination thereof, a composition comprising as an active ingredient an extract of *Allium* species comprising quercetin, an extract of *Citrus* species, an extract of *Paullinia* species and an extract of *Theobroma* species.

2. A method for the management of the cancer and for the treatment of cancer-related fatigue according to claim 1, wherein the composition contains the extract of the *Allium* species comprising quercetin, the extract of the *Citrus* species, an atomized extract of the *Paullinia* species and an atomized extract of the *Theobroma* species.

3. A method for the management of the cancer and for the treatment cancer-related fatigue according to claim 1, wherein the composition comprises: from 30% to 93% by weight of the extract of the *Allium* species comprising quercetin, from 3% to 33% by weight of the extract of the *Citrus* species, from 0.10% to 2.5% by weight of the extract of the *Pauffinia* species, and from 0.10% to 2.5% by weight of the extract of the *Theobroma* species, based on the total weight of the four active ingredients.

4. A method for management of cancer and for treatment of cancer-related fatigue in a subject in need thereof, the method comprising:
    administering to the subject, by an oral route, a topical route, a parenteral route, an intra-tumoral injection, or a combination thereof, a composition consisting of an extract of *Allium* species comprising quercetin, an extract of *Citrus* species, an extract of *Pauffinia* species, and an extract of *Theobroma* species.

* * * * *